(12) United States Patent
Ortega Jimenez et al.

(10) Patent No.: US 11,304,670 B2
(45) Date of Patent: Apr. 19, 2022

(54) MULTIFUNCTIONAL RADIOGRAPHY, TOMOGRAPHY AND FLUOROSCOPY DEVICE

(71) Applicant: Sociedad Española de Electromedicina y Calidad S.A, Madrid (ES)

(72) Inventors: Jose Maria Ortega Jimenez, Madrid (ES); Juan Manuel Arco Casanova, Madrid (ES)

(73) Assignee: Sociedad Española de Electromedicina y Calidad S.A, Madrid (ES)

(*) Notice: Subject to any disclaimer, the term of this patent is extended or adjusted under 35 U.S.C. 154(b) by 46 days.

(21) Appl. No.: 16/958,036

(22) PCT Filed: Dec. 28, 2018

(86) PCT No.: PCT/ES2018/070837
§ 371 (c)(1),
(2) Date: Jun. 25, 2020

(87) PCT Pub. No.: WO2019/129912
PCT Pub. Date: Jul. 4, 2019

(65) Prior Publication Data
US 2021/0059620 A1    Mar. 4, 2021

(30) Foreign Application Priority Data

Dec. 28, 2017  (ES) .................................. P201731485

(51) Int. Cl.
*A61B 6/00*   (2006.01)
*A61B 6/03*   (2006.01)
(Continued)

(52) U.S. Cl.
CPC ............ *A61B 6/4441* (2013.01); *A61B 6/032* (2013.01); *A61B 6/0407* (2013.01); *A61B 6/06* (2013.01);
(Continued)

(58) Field of Classification Search
CPC ....... A61B 6/487; A61B 6/466; A61B 6/4452; A61B 6/4441; A61B 6/06; A61B 6/0407; A61B 6/032
See application file for complete search history.

(56) References Cited

U.S. PATENT DOCUMENTS 3,838,287 A    9/1974  Barrett
5,995,581 A   11/1999  Ozaki
(Continued)

FOREIGN PATENT DOCUMENTS

DE    102013220204 A1   4/2015
DE    102015222076 A1   5/2017
(Continued)

OTHER PUBLICATIONS

DE102013220204 English Translation (Year: 2015).*

*Primary Examiner* — Dani Fox
(74) *Attorney, Agent, or Firm* — Hayes Soloway P.C.

(57) ABSTRACT

The invention relates to radiographic equipment comprising a height-adjustable board, a C-shaped arch, disposed transversally to the greater dimension of the board, said board being housed within the internal space defined between the two free extremities of the arch. The arch is slidingly mounted on a column by means of a connecting element in such a way that as the arch rotates around an imaginary rotational axis it causes the connecting element to slide or roll throughout the extension of the arch. It further comprises a rail extending parallel to the greater dimension of the board, on which the column rests. The arch features at its (Continued)

lower extremity an x-ray receiver and at its upper extremity an x-ray emission assembly.

11 Claims, 7 Drawing Sheets

(51) Int. Cl.
*A61B 6/04* (2006.01)
*A61B 6/06* (2006.01)
*G01T 1/28* (2006.01)

(52) U.S. Cl.
CPC .............. *A61B 6/466* (2013.01); *A61B 6/487* (2013.01); *G01T 1/28* (2013.01)

(56) References Cited

U.S. PATENT DOCUMENTS

| | | | |
|---|---|---|---|
| 2002/0085681 A1* | 7/2002 | Jensen | A61B 6/463 378/197 |
| 2005/0129181 A1 | 6/2005 | Shinoda et al. | |
| 2006/0023830 A1* | 2/2006 | Schomberg | A61B 6/4085 378/4 |
| 2008/0118023 A1 | 5/2008 | Besson et al. | |
| 2013/0345543 A1 | 12/2013 | Steibel et al. | |
| 2017/0000675 A1 | 1/2017 | Hight et al. | |

FOREIGN PATENT DOCUMENTS

| | | |
|---|---|---|
| WO | 2010128417 A1 | 11/2010 |
| WO | 2016032133 A1 | 3/2016 |

\* cited by examiner

MULTIFUNCTIONAL RADIOGRAPHY, TOMOGRAPHY AND FLUOROSCOPY DEVICE

CROSS-REFERENCE TO RELATED APPLICATIONS AND PRIORITY

This patent application claims priority from PCT Patent Application No. PCT/ES2018/070837 filed Dec. 28, 2018, which claims priority from Spanish Patent Application No. ES P 201731485 filed Dec. 28, 2017. Each of these patent applications are herein incorporated by reference in their entirety.

OBJECT OF THE INVENTION

The object of the present invention, as revealed in the title, is universal equipment for the performance of radiography, tomography and fluoroscopy enabling the taking of conventional two-dimensional radiographs, three-dimensional tomographs and fluoroscopic images.

The present invention is characterised by the particular characteristics presented by each of the elements forming part the equipment and the interconnection between the same, in such a way that the same is constituted as a versatile item of equipment providing multiple functions, such as the performance of two-dimensional radiographs and three-dimensional tomographs, and likewise fluoroscopy.

Therefore, the present invention is included in the field of x-ray machines designed for the examination of both humans and animals.

BACKGROUND OF THE INVENTION

Many items of equipment for the performance of x-ray radiographs have been developed, such as:
- Equipment with a fixed focal length, where the radiation tube support has 2 options, as a stretcher-like table or the option of a height-adjustable table, also of different lengths and with an electronic brake.
- Conventional equipment with a variable focal length, which may be coupled to a stretcher or to a height-adjustable table.
- Conventional equipment with a variable focal length and a displaceable column. The vertically sliding column provides the advantage of the possibility of performing radiographs on extremities "under load", studies which would be impossible to perform with the patient on the table. Likewise, the displacement of the column toward the lateral extremities of the table makes possible on-table lateral examinations, with the x-ray beam parallel to the surface thereof.
- There exist other items of equipment with which it is possible to perform oblique examinations with a greater range of projection angles than the Variable Focal Length System.

All the above equipment presents aspects that are amenable to improvement, in some cases because they do not permit the execution of 2D radiographs throughout the length of the patient, enabling the viewing of the entirety of the same; in others it is not possible to perform 3D tomography, in others because it is not possible to extend the field of view and perform large-scale 3D tomographs.

Furthermore, conventional equipment generally have considerable dimensions and requires extensive spaces for its installation.

Moreover, conventional equipment is known which present totally enclosed housings within which the patient is disposed to obtain images; this does not enable simple access to the patient during the performance of the radiograph, in addition to entailing, in general, discomfort for the patients.

DESCRIPTION OF THE INVENTION

The object of the present invention is equipment such as that described below and whose essential nature is revealed in the first claim; it being possible to perform both two-dimensional radiographs and three-dimensional tomographs, and also fluoroscopic images, it also being a compact item of equipment which does not require large spaces for its installation, and which in turn enables simple access to the patient during the obtaining of the images.

The equipment for the performance of radiography, tomography and fluoroscopy comprises:
- A height-adjustable board. This may feature legs to adjust the height, and/or may be a floating board, which may be moved in all directions on a single plane,
- A C-shaped frame or arch disposed transversally to the greater dimension of the board, the board being housed within the internal space comprised between the two free extremities of the arch. The arch is installed upon a column whose base rests on a rail extending parallel to the greater dimension of the board, in such a way that the arch may be displaced along the rail in a longitudinal direction with regard to said board.
- The arch and the column are slidingly connected via a connecting element that the column comprises at its upper extremity; said element may be a roller bearing; in such a way that as the arch rotates with regard to an imaginary axis parallel to the greater dimension of the board, the connecting element slides or rolls throughout the extension of the arch.
- The C-shaped arch comprises:
- At its lower extremity, a "flat panel" or digital x-ray receiver housed beneath the board and which moves solidarily with the arch,
- At its upper extremity, an x-ray emission assembly formed by an x-ray tube and a collimator, this being a number of mobile lead plates which limit the field to be irradiated.

A connecting element that enables the linking of the upper extremity of the C-shaped arch to the x-ray emission assembly. Optionally, the emission assembly may feature an asymmetric collimator comprising a number of blinds which may move independently and asymmetrically as required, in order to prevent the undesired irradiation of areas.

The "flat panel" or receiver presents the possibility of lateral displacement in a direction transversal to the greater dimension of the board and toward both sides, this enabling an increase in the field of view for tomography.

Furthermore, the possibility of longitudinal displacement of the C-shaped arch along the board, thanks to the rails upon which the column supporting the arch runs, enables the execution of radiographs of the entire length of the patient.

The arch is configured so as to rotate in both directions (clockwise and anti-clockwise) with regard to an imaginary axis parallel to the greater dimension of the board.

Additionally, the arch may feature means which enables it to rotate in such a way that it may remain horizontal with regard to the plane of the floor; furthermore, the column further comprises means enabling it, in addition to its horizontal displacement, to be displaced or rotated with regard to a vertical axis passing through the column itself in such a way as to permit the arch to be disposed in a horizontal position without interfering with the table.

Thanks to the combined rotation of the arch with regard to an imaginary axis parallel to the surface of the board and which passes through the point of attachment to the column, and to the possibility that the column may be moved or rotated in such a way that the rotation of the arch does not interfere with the table, it is possible to perform radiographs with the patient in a standing position as well as lying down, in both positions both two-dimensionally and three-dimensionally, and encompassing the entire body in a vertical position.

With the equipment it is possible to perform real-time fluoroscopy, as the "flat panel" or receiver enables the performance of high-speed sequential captures.

Thus, by means of the equipment described it is possible to:
  Perform 2D radiographs and 3D tomographs of the entire length of the patient, be said patient animal or human, either under load or lying down.
  Perform axial tomographs of a patient with no need to perform a complete rotation of the arch.
  Operate with a greater field of view in tomographic images.
  Perform real-time fluoroscopy.

Furthermore, this is compact equipment which does not require large spaces for its installation; it enables access to the patient during the obtaining of images; it presents an ample field of view for the performance of radiographs on patients (be they animal or human) of any size, and further enables simple accommodation of the patient on the board, this being height-adjustable.

EXPLANATION OF THE FIGURES

As a supplement to the description made herein, and for the purpose of aiding a better understanding of the characteristics of the invention, in accordance with a preferred example of a practical embodiment of the same, a set of drawings is attached as an integral part of said description wherein, by way of illustration and not limitation, the following is portrayed.

PREFERRED EMBODIMENT OF THE INVENTION

In the light of the figures, a preferred embodiment of the proposed invention may be found below.

Figure 1:
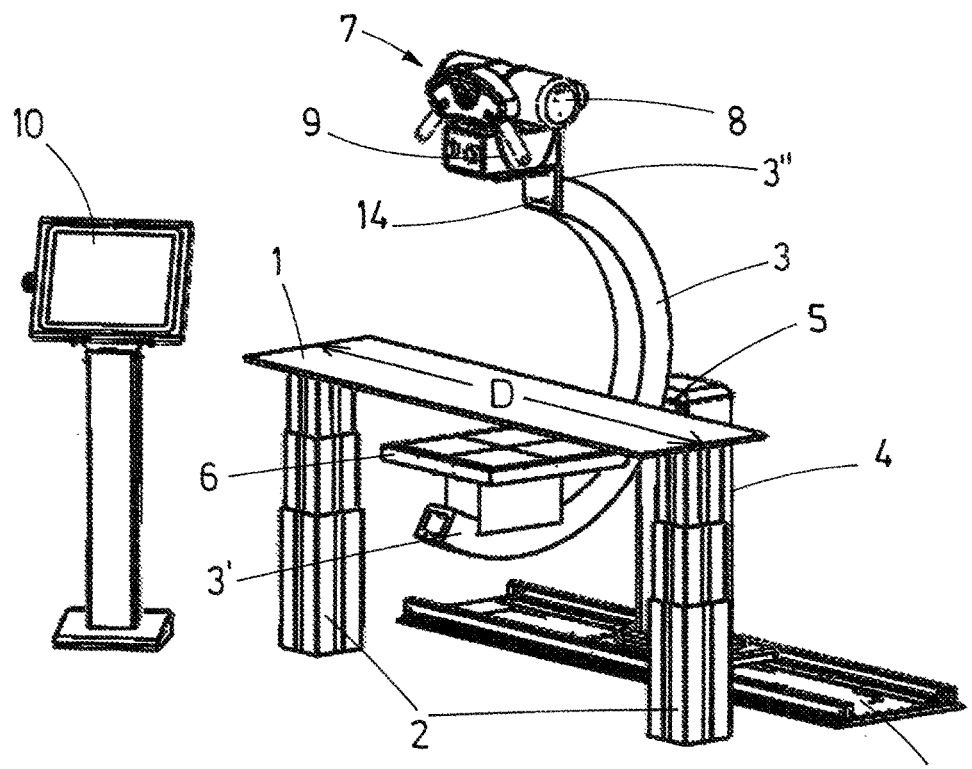
FIG. 1.—Portrays a perspective view of radiographic equipment such as the object of the present invention.

In FIG. 1 a radiography x-ray machine may be observed; this comprises, among other elements, a board (1) supported by a number of height-adjustable motorised legs (2), enabling the board (1) to float with regard to the remainder of the equipment, and to move on the plane thereof. It further comprises a C-shaped arch (3) disposed transversally to the greater dimension (D) of the board (1), in such a way that the latter is housed within the internal space comprised between the two free extremities (3' and 3") of the arch (3).

The arch (3) is slidingly installed on a column (4) by means of a transmission mechanism (5), which may be a linear guide or a roller bearing. Said transmission mechanism (5) or roller bearing is configured in order to slide or roll along the extension of the arch (3) while the latter rotates with regard to an imaginary rotational axis (13) parallel to the greater dimension (D) of the board (1).

The column (4) in turn is disposed on a rail (12) located parallel to the greater dimension (D) of the board, along which the column (4), attached to the arch (3) is displaced longitudinally with regard to said board (1).

The C-shaped arch (3) presents at its lower extremity (3') a "flat panel" or x-ray receiver (6), while at its upper extremity it holds the x-ray emission assembly (7), comprised of an x-ray tube (8) and a collimator (9). The arch (3) is linked to the x-ray emission assembly (7) by means of a connecting element (14).

The x-ray emission assembly may include a screen or monitor (10) for the viewing of the images captured. The screen or monitor may also be disposed beside the equipment, as portrayed in FIG. 1, or may be installed on the arch at the extremity where the x-ray tube is located.

Figure 2:
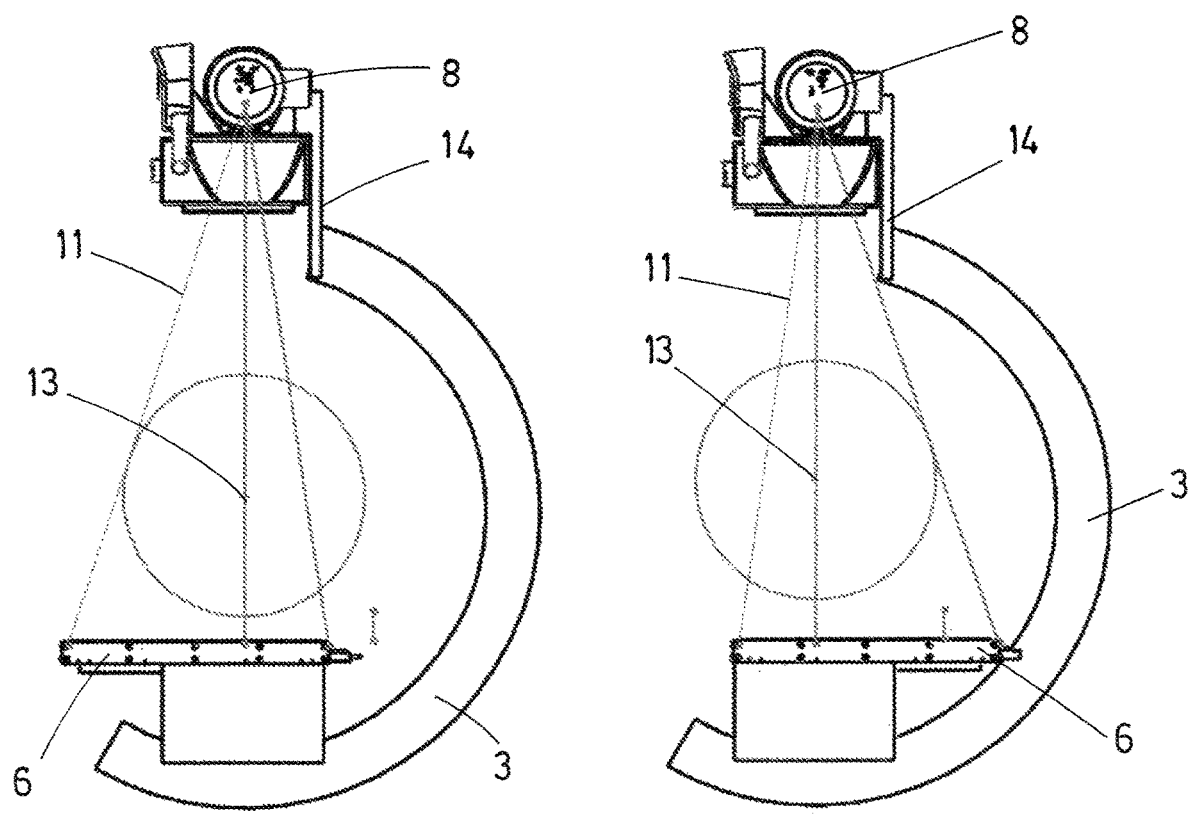
FIG. 2.—Portrays two schematic lateral views of the C-shaped arch with the "flat panel" or receiver displaced laterally in a direction transversal to that of the board.
Figure 3:
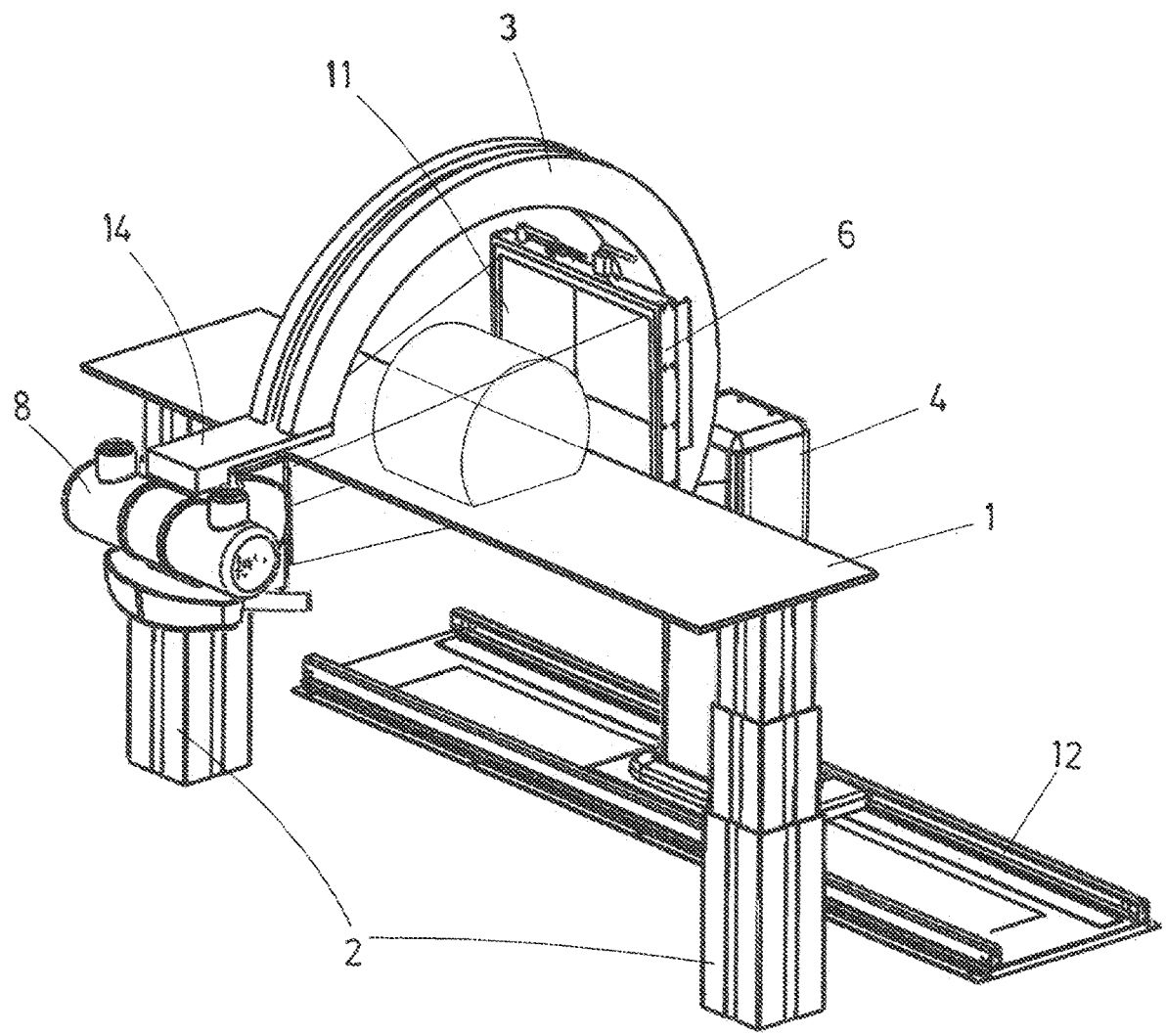
FIG. 3.—Portrays a perspective view of radiographic equipment such as the object of the invention while it performs the capture of images (the arch appears completely rotated in one of the directions of rotation).

FIG. 2 portrays one of the particular characteristics of the equipment, this being the possibility that the "flat panel" (6) or receiver is configured so as to make possible its lateral displacement in an orientation transversal to the greater dimension of the board, and in both directions, a feature which enables an increase in the field of view (11) in tomography.

Furthermore, the "flat panel" or receiver is configured to take several photographs simultaneously, enabling the performance of real-time fluoroscopy.

The arch (3) is configured to rotate in both directions around an imaginary rotational axis (13) parallel to the greater dimension (D) of the board (1), in such a way that it enables the obtaining of the complete image of the patient without the need to perform a complete 360° rotation of the C-shaped arch (3).

Figure 4:
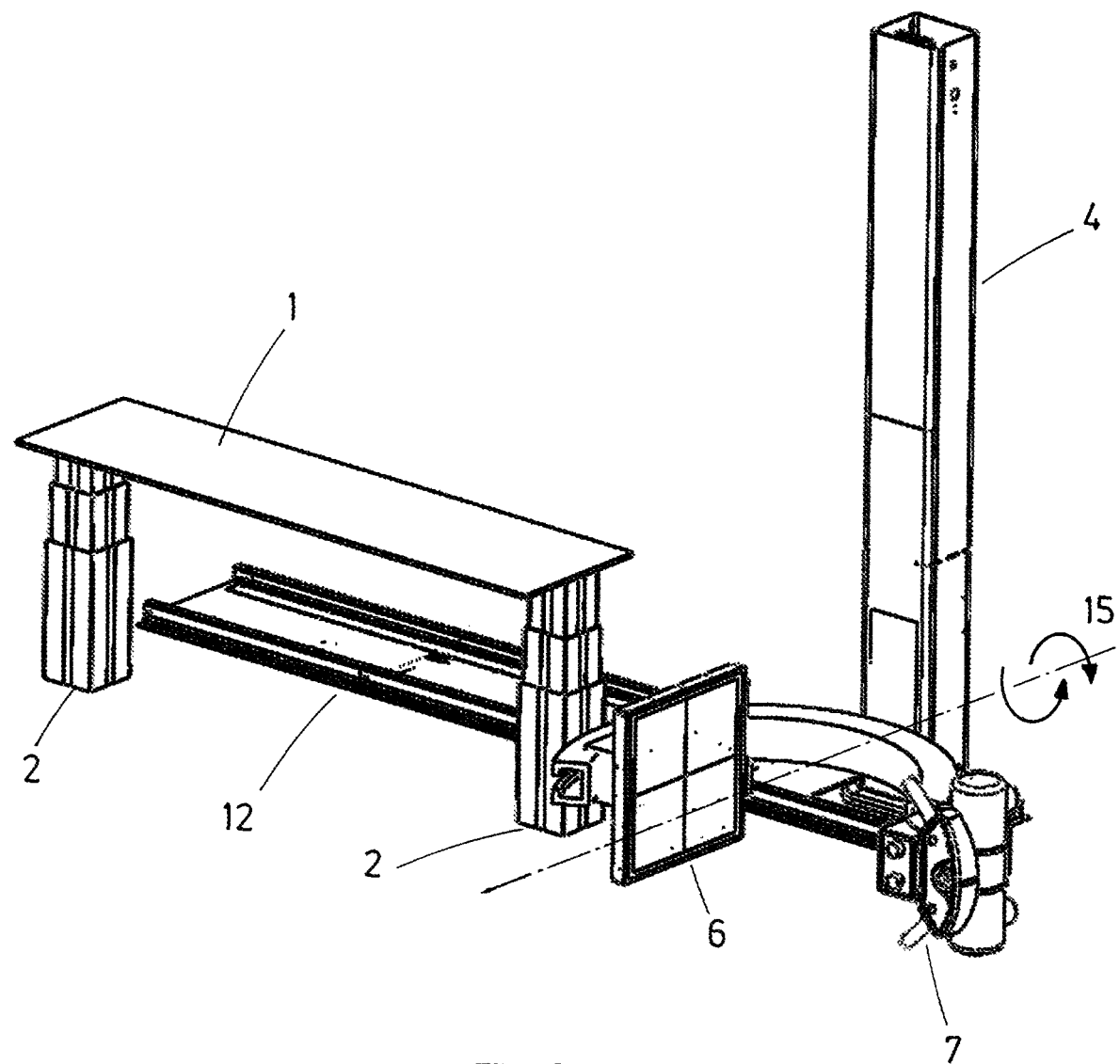
FIGS. 4 to 7 portray an additional embodiment wherein the guide rail presents a length greater than the length of the table, and wherein the arch offers the possibility of rotation around a horizontal axis.

FIG. 4 portrays an additional embodiment of the invention wherein the guide rail (12) presents a length greater than the dimension of the table, formed by the board (1) and the legs (2), and, furthermore, the arch (3) presents the particular characteristic of the possibility of rotation with regard to a horizontal axis (15) with regard to the plane of the floor, and passing through the point of attachment to the column (4), where the column (4) presents a greater height than that portrayed in the previous embodiments.

The combination of all of the above characteristics together enables the performance of 2D-3D radiographs with a patient in a vertical position.

Figure 5:
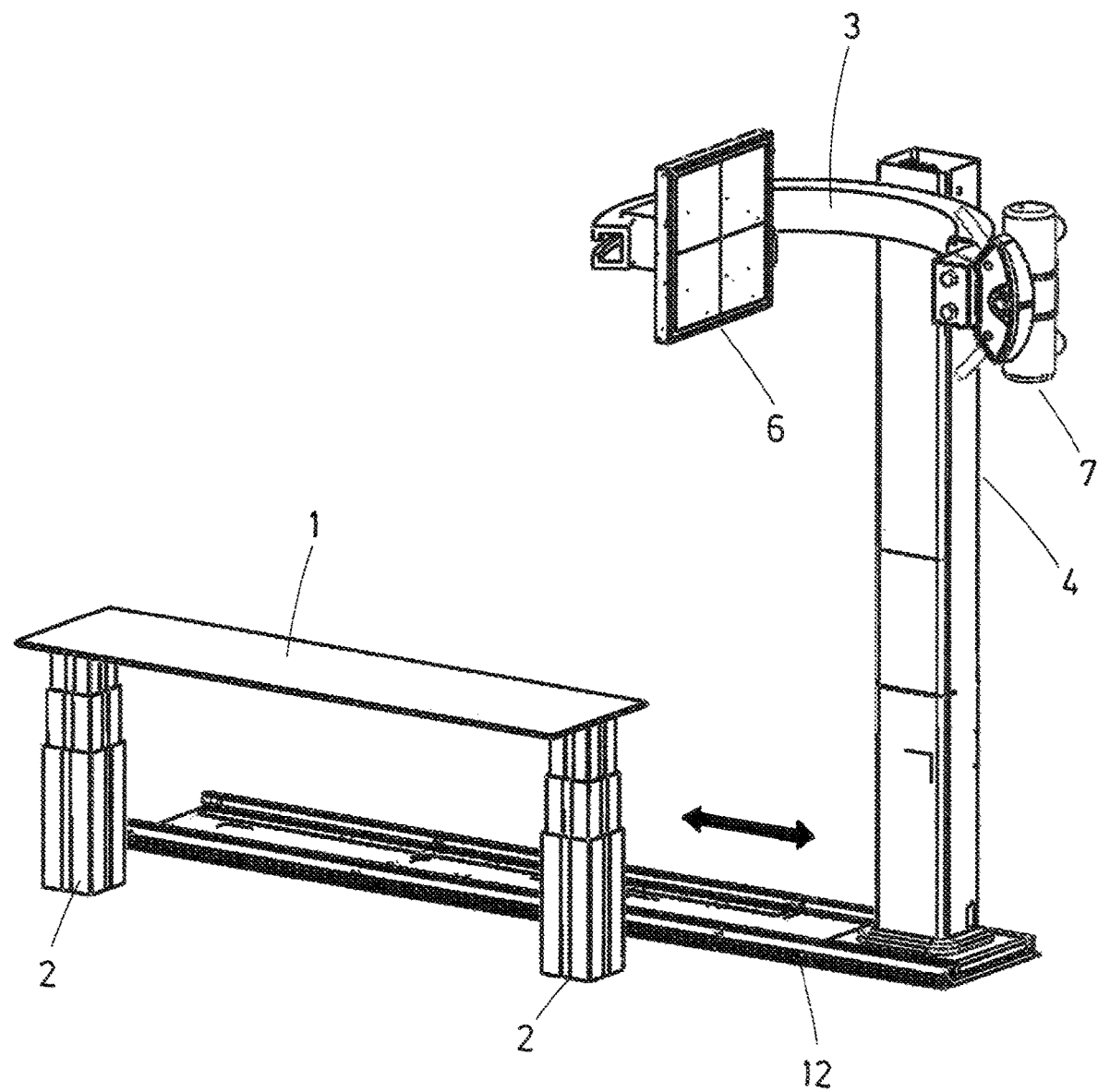

FIG. 4 portrays the arch (3) at the lowest position on the column (4), while FIG. 5 portrays the arch (3) at the highest position.

Figure 6:
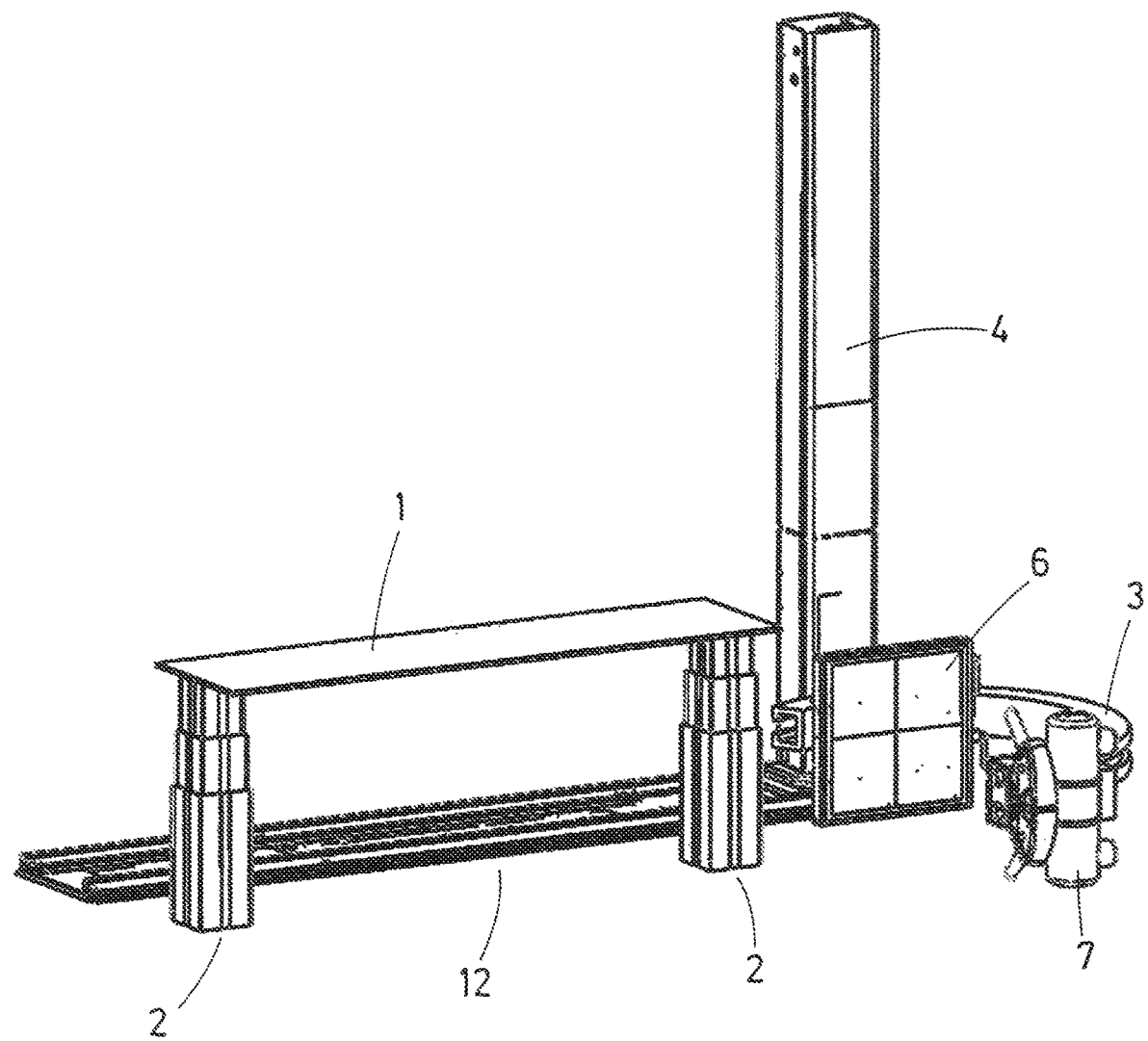

FIG. 6 portrays the arch (3) at the lowest position possible, where the arch has been moved along its point of connection, with the column (4) close to the receiver (6).

Figure 7:
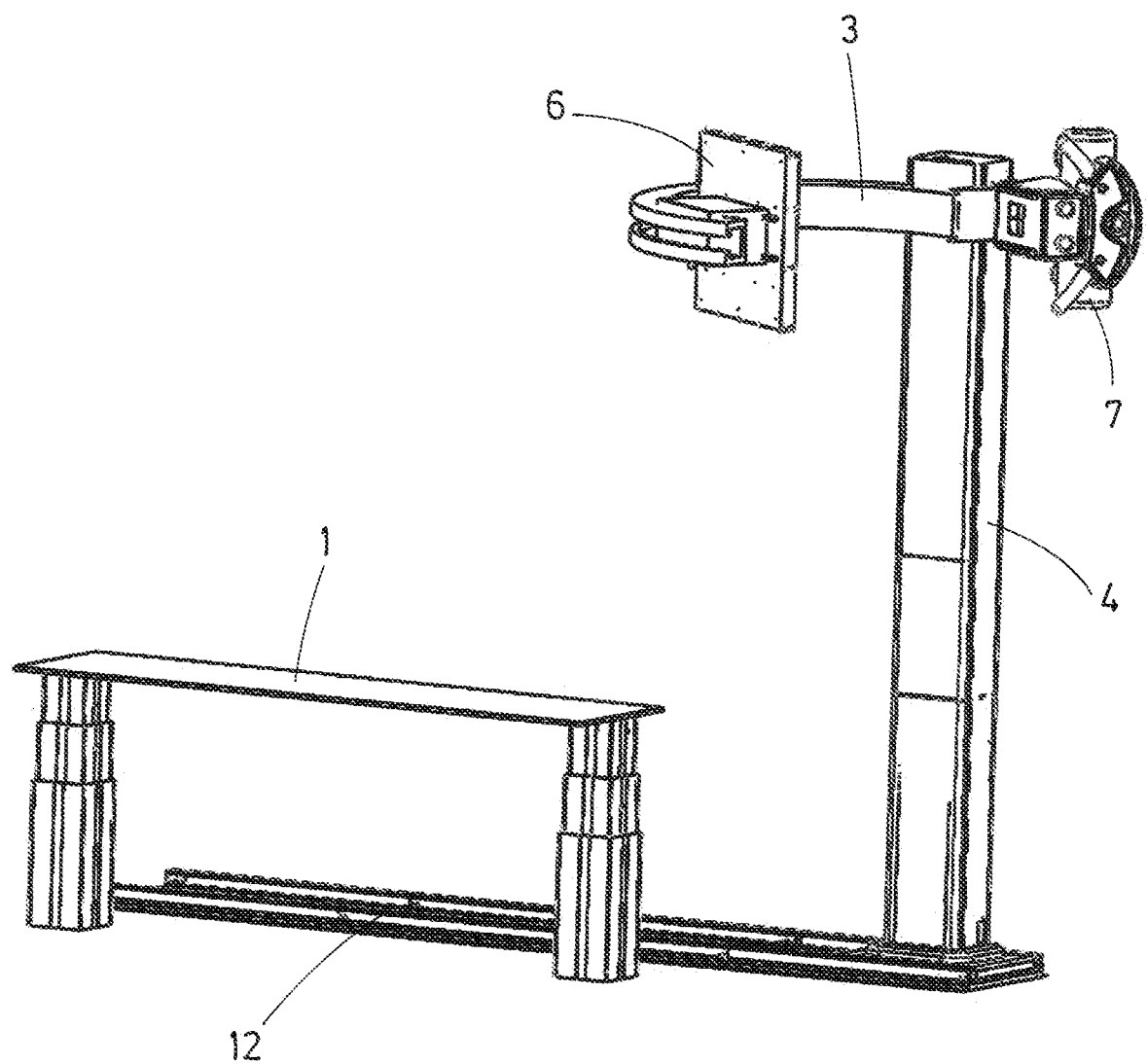

FIG. 7 portrays the arch (3) at the highest position on the column (4), where the arch has been moved along its point of connection, with the column (4) close to the x-ray emission assembly (7).

Figure 8:
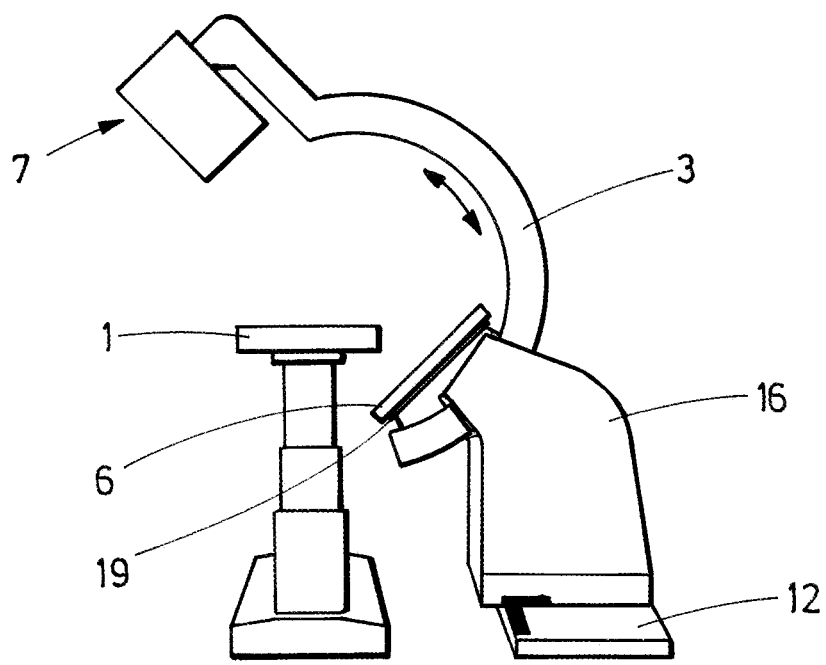
FIG. 8.—Portrays a perspective view of an alternative embodiment of the equipment of the invention wherein the column is replaced by a body that includes motorisation and transmission mechanisms that facilitate the movements of the frame.

According to another embodiment shown in FIG. 8, the multi-purpose equipment for the performance of radiography, tomography and fluoroscopy comprises:

a table provided with a board (1) that has longer sides and shorter sides and height-adjustable legs that support the board (1) wherein the board (1) is vertically displaceable, a frame (3) that is substantially C-shaped, which is disposed transversally to the longer side of the board (1), which has rotational movement in both directions around a central rotation axis perpendicular to the plane of the frame (3), which has an upper extremity and a lower extremity, a radiation emission assembly (7) disposed in the upper extremity of the frame (1) that incorporates an x-ray tube and a collimator, an x-ray detection assembly disposed in the lower extremity of the frame (3), and a first body (16) on which the frame is mounted with the capacity of rotational sliding, which incorporates a first drive unit and a first transmission mechanism that cause the rotational sliding movement of the frame (3).

Furthermore, it is observed in this same FIG. 8 that the equipment comprises a rail (12) that can be coupled to the floor and parallel to the longer side of the board (1), on which the first body (16) and the frame (3) are displaced in a direction parallel to the longer side of the board (1).

The equipment shown in FIG. 8 is mostly known because the x-ray tube of the radiation emission assembly is intended to perform 2D and 3D radiographs of the patient and real-time fluoroscopy, and the x-ray detection assembly comprises a dynamic flat panel (6) intended to receive x-rays for performing 2D and 3D radiographs and taking various simultaneous photographs to perform real-time fluoroscopy.

In the embodiment portrayed in FIG. 8, the first body (16) internally comprises a second drive unit and a second transmission mechanism that facilitate the guided displacement of the first body (16) on the rail (12).

Figure 9:
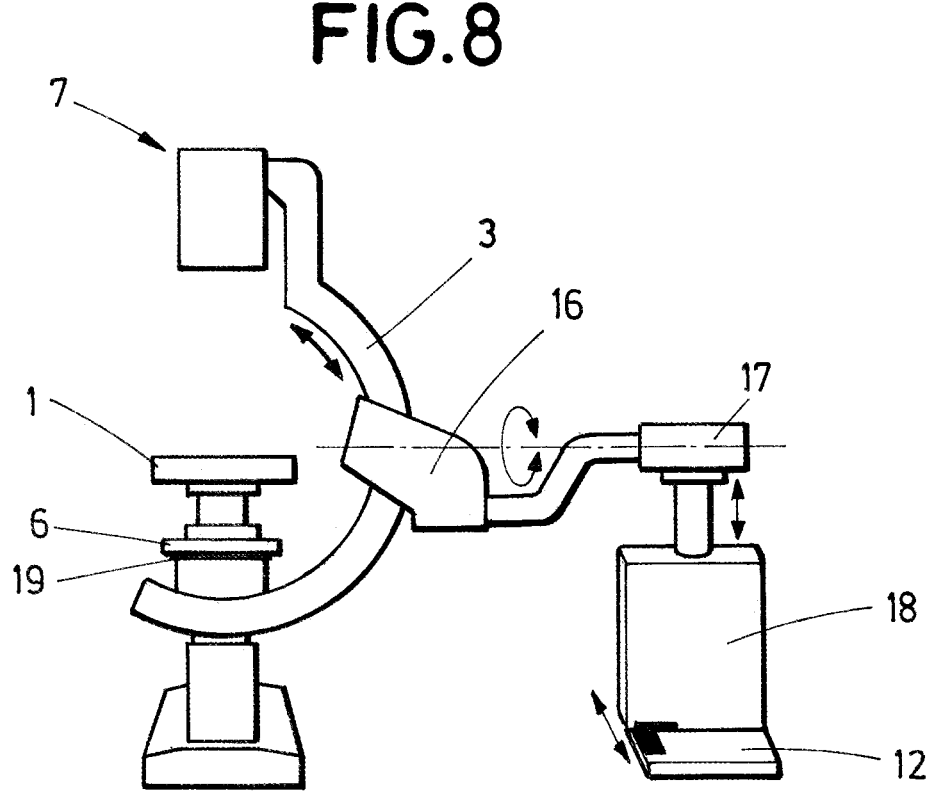
FIG. 9.—Portrays a view of another embodiment of the invention wherein the column is replaced by bodies with motorisation and mechanisms that enable additional movements of the frame.

Furthermore, it shows another embodiment of the equipment portrayed in FIG. 9, wherein, unlike FIG. 8, the first body (16) is mounted in a rotational mechanism (17) that facilitates the total rotation of the first body (16) and frame (3) around a horizontal axis contained in the plane of the frame (3); moreover, it is observed that the equipment comprises a second body (18) with respect to which the height of the rotational mechanism (17) can be displaced and therefore, the first body (16) and the frame (3), the second body (18) having a third drive unit and a third transmission mechanism that facilitate the guided displacement of the second body (18) on the rail (12) in a direction parallel to the longer side of the board (1).

In both cases, the dynamic flat panel (6) is mounted on the lower end of the frame (3) with intermediation of a structure (19) that enables the displacement of the board (1) in a direction perpendicular to the plane of the frame (3).

The invention claimed is:

1. A multi-purpose equipment for radiography, tomography and fluoroscopy comprising:

a table provided with a board that has longer sides and shorter sides, wherein the board is vertically displaceable, a frame that is substantially C-shaped disposed transversally to the longer side of the board, which has a rotational movement in both directions around a central rotation axis perpendicular to the plane of the frame, said frame being provided with an upper extremity and a lower extremity, a first body on which the frame is mounted which incorporates a first drive unit and a first transmission mechanism that cause the rotational sliding movement of the frame, a radiation emission assembly disposed in the upper extremity of the frame, that comprises an x-ray tube and a collimator, an x-ray detection unit disposed in the lower extremity of the frame, a rail that can be coupled to the floor and parallel to the longer side of the board on which the first body and the frame can be displaced in a direction parallel to the longer side of the board, wherein the x-ray tube of the radiation emission assembly is intended to perform 2D radiographs and 3D tomographs of the patient and real-time fluoroscopy, and the x-ray detection unit comprises a dynamic flat panel intended to receive x-rays for performing 2D radiographs and 3D tomographs and acquiring various sequential images to perform real-time fluoroscopy, and wherein the equipment further comprises a connecting element extending outward from the upper extremity of the frame connecting the radiation emission assembly to said upper extremity.

2. The multi-purpose equipment for radiography, tomography and fluoroscopy of claim 1, wherein the collimator is asymmetric, comprising a number of blinds which may move independently and asymmetrically as required, in order to prevent the irradiation of undesired areas.

3. The multi-purpose equipment for radiography, tomography and fluoroscopy, as claimed in claim 1, wherein it further comprises a screen or monitor for the viewing of the images captured.

4. The multi-purpose equipment for radiography, tomography and fluoroscopy of claim 3, wherein the screen or monitor is mounted on the arch at the extremity where the x-ray tube is located.

5. The multi-purpose equipment for radiography, tomography and fluoroscopy according of claim 1, wherein the first body comprises a second drive unit and a second transmission mechanism that facilitate the guided displacement of the first body on the rail.

6. The multi-purpose equipment for radiography, tomography and fluoroscopy of claim 1, wherein it further comprises a rotational mechanism on which the first body is mounted that facilitates the total rotation of the first body and frame around a horizontal axis contained in the plane of the frame; moreover, it comprises a second body with respect to which the rotational mechanism can be displaced in height and therefore the first body and the frame, the second body having a third drive unit and a third transmission mechanism that facilitate the guided displacement of the second body on the rail in a direction parallel to the longer side of the board.

7. The multi-purpose equipment for radiography, tomography and fluoroscopy of claim 1, wherein the dynamic flat panel is mounted on the lower end of the frame with intermediation of a structure that enables the displacement of the flat panel in a direction perpendicular to the plane of the frame and in both directions in order to increase the field of view in tomography.

8. The multi-purpose equipment for radiography, tomography and fluoroscopy of claim 1 wherein the first body comprise a column where in the arch is slidingly installed on, by means of the transmission mechanism.

9. The multi-purpose equipment for radiography, tomography and fluoroscopy according to claim 8 wherein the transmission mechanism is a roller bearing.

10. The multi-purpose equipment for radiography, tomography and fluoroscopy of claim 1, wherein the table is fitted with height-adjustable legs that support the board.

11. The multi-purpose equipment for radiography, tomography and fluoroscopy of claim 1 wherein the board is a floating board.

* * * * *